(12) United States Patent
Nuggehalli et al.

(10) Patent No.: US 9,451,170 B2
(45) Date of Patent: Sep. 20, 2016

(54) IMAGE ACQUISITION AND MANAGEMENT USING A REFERENCE IMAGE

(71) Applicants: Jayasimha Nuggehalli, Sunnyvale, CA (US); James Woo, Los Altos, CA (US)

(72) Inventors: Jayasimha Nuggehalli, Sunnyvale, CA (US); James Woo, Los Altos, CA (US)

(73) Assignee: Ricoh Company, Ltd., Tokyo (JP)

( * ) Notice: Subject to any disclaimer, the term of this patent is extended or adjusted under 35 U.S.C. 154(b) by 15 days.

(21) Appl. No.: 14/543,712

(22) Filed: Nov. 17, 2014

(65) Prior Publication Data

US 2016/0142637 A1    May 19, 2016

(51) Int. Cl.
*H04N 5/232* (2006.01)
*H04N 5/262* (2006.01)
*G06T 7/00* (2006.01)
*G06K 9/32* (2006.01)
*G06K 9/62* (2006.01)
*A61B 5/00* (2006.01)

(52) U.S. Cl.
CPC ........... *H04N 5/23293* (2013.01); *A61B 5/445* (2013.01); *G06K 9/32* (2013.01); *G06K 9/62* (2013.01); *G06T 7/0016* (2013.01); *H04N 5/23222* (2013.01); *H04N 5/2621* (2013.01); *G06T 2207/30088* (2013.01)

(58) Field of Classification Search
CPC ..................... H04N 5/23206; H04N 5/23216; H04N 5/23222; H04N 5/23293; H04N 5/2621; G06T 1/0007; G06T 7/0016; G06T 7/003; G06T 7/0044; G06T 7/0065; G06T 2207/10016; G06T 2207/10024; G06T 2207/30004; G06T 2207/30088; G06K 9/32; G06K 9/62
See application file for complete search history.

(56) References Cited

U.S. PATENT DOCUMENTS

| 5,732,401 | A  | 3/1998  | Conway    |
|-----------|----|---------|-----------|
| 7,150,399 | B2 | 12/2006 | Barrus    |
| 7,606,863 | B2 | 10/2009 | Ogasawara |
| 7,991,837 | B1 | 8/2011  | Tahan     |
| 8,330,831 | B2 | 12/2012 | Steinberg |
| 8,798,401 | B1 | 8/2014  | Johnson   |
| 2002/0088000 | A1 | 7/2002 | Morris  |
| 2003/0023623 | A1 | 1/2003 | Horvitz |

(Continued)

FOREIGN PATENT DOCUMENTS

WO    WO 2014/125831 A1    8/2014

OTHER PUBLICATIONS

European Patent Office, "Search Report" in application No. 15194724.9—1903, dated Apr. 19, 2016, 10 pages.

(Continued)

*Primary Examiner* — Dennis Hogue
(74) *Attorney, Agent, or Firm* — Hickman Palermo Becker Bingham LLP; Edward A. Becker

(57) ABSTRACT

A reference image of one or more objects is displayed on the display of a mobile device in a manner that allows a user of the mobile device to simultaneously view the reference image and a preview image of the one or more objects currently in a field of view of a camera of the mobile device. An indication is provided to the user of the mobile device whether the camera of the mobile device is currently located within a specified amount of a distance at which the reference image was acquired. In response to a user request, the camera acquires a second image of the one or more objects and optionally a distance between the camera and the one or more objects at the time the second image was acquired is recorded. An image management application provides various functionalities for accessing and managing image sequences.

20 Claims, 15 Drawing Sheets

(56) References Cited

U.S. PATENT DOCUMENTS

| | | | |
|---|---|---|---|
| 2003/0063771 A1 | 4/2003 | Morris | |
| 2003/0225325 A1* | 12/2003 | Kagermeier | A61B 6/08 600/407 |
| 2004/0019270 A1* | 1/2004 | Takeuchi | A61B 8/14 600/407 |
| 2004/0201756 A1* | 10/2004 | VanBree | H04N 5/222 348/239 |
| 2004/0243822 A1 | 12/2004 | Buchholz | |
| 2006/0018652 A1* | 1/2006 | Sugiura | G03B 17/02 396/213 |
| 2006/0059253 A1 | 3/2006 | Goodman | |
| 2007/0030363 A1* | 2/2007 | Cheatle | H04N 1/00183 348/239 |
| 2008/0086305 A1 | 4/2008 | Lewis | |
| 2009/0077129 A1 | 3/2009 | Blose | |
| 2009/0235334 A1 | 9/2009 | Park | |
| 2009/0260060 A1 | 10/2009 | Smith | |
| 2009/0292930 A1 | 11/2009 | Marano | |
| 2010/0026816 A1 | 2/2010 | Bergstrom | |
| 2010/0100941 A1 | 4/2010 | Eom | |
| 2010/0205553 A1* | 8/2010 | Haigh | G01J 5/02 715/769 |
| 2010/0250497 A1 | 9/2010 | Redlich | |
| 2010/0304720 A1* | 12/2010 | Lucero | H04N 1/00127 455/414.1 |
| 2011/0129120 A1 | 6/2011 | Chan | |
| 2011/0242282 A1 | 10/2011 | Arai | |
| 2011/0279697 A1* | 11/2011 | Shingu | H04N 5/2621 348/222.1 |
| 2012/0078113 A1 | 3/2012 | Whitestone et al. | |
| 2012/0106795 A1 | 5/2012 | Farrer | |
| 2013/0027569 A1 | 1/2013 | Parulski | |
| 2013/0038759 A1 | 2/2013 | Jo et al. | |
| 2013/0051611 A1 | 2/2013 | Hicks | |
| 2013/0141362 A1 | 6/2013 | Asanuma | |
| 2013/0212094 A1 | 8/2013 | Naguib | |
| 2014/0095632 A1 | 4/2014 | Grosz | |
| 2014/0226052 A1 | 8/2014 | Kang et al. | |
| 2015/0095433 A1 | 4/2015 | Grossman | |
| 2015/0163206 A1 | 6/2015 | McCarthy | |
| 2016/0142611 A1 | 5/2016 | Nuggehalli et al. | |

OTHER PUBLICATIONS

U.S. Appl. No. 14/641,268, filed Mar. 6, 2015, Office Action, Mar. 22, 2016.

U.S. Appl. No. 14/641,264, filed Mar. 6, 2015, Office Action, Apr. 21, 2016.

U.S. Appl. No. 14/619,550, filed Feb. 11, 2015, Office Action, Apr. 21, 2016.

U.S. Appl. No. 14/543,725, filed Nov. 17, 2014, Office Action, Feb. 26, 2016.

TechNet, How to Share and Set Permissions for Folders and Files Windows Xp, dated Dec. 2011, https://technet.microsoft.como/en-us/library/bb456988(d=printer). Aspx, 2 pages.

U.S. Appl. No. 14/543,725, filed Nov. 17, 2014, Advisory Action, Aug. 4, 2016.

* cited by examiner

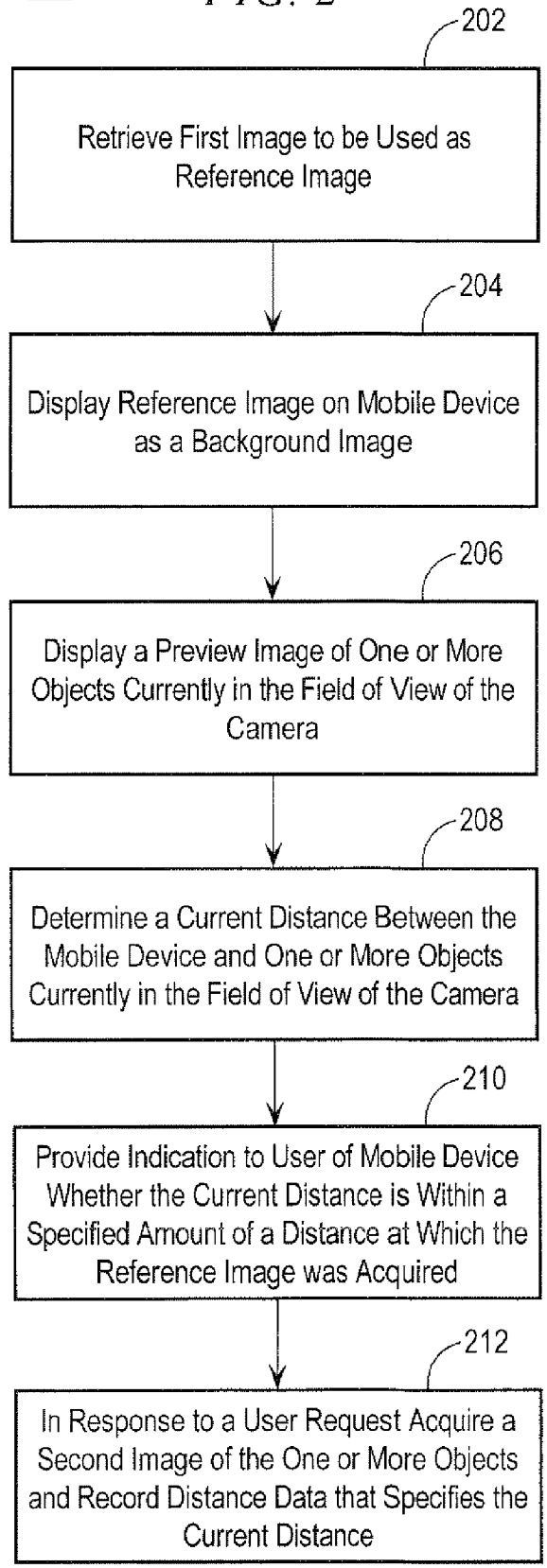

500

| Memo Data |
|---|
| Patient ID |
| Employee ID |
| Wound Location |
| Anatomy ID |
| Wound Distance |
| Date |
| Department |
| Doctor ID |
| Status |

FIG. 7A

IMAGE ACQUISITION AND MANAGEMENT USING A REFERENCE IMAGE

RELATED APPLICATION DATA AND CLAIM OF PRIORITY

This application is related to U.S. patent application Ser. No. 14/543,725 entitled IMAGE ACQUISITION AND MANAGEMENT USING A REFERENCE IMAGE, filed Nov. 17, 2014, the contents all of which are incorporated by reference in their entirety for all purposes as if fully set forth herein.

FIELD OF THE INVENTION

Embodiments relate generally to acquiring and managing images.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

An increasing number of mobile devices, such as smartphones and tablet computers, are equipped with cameras. This makes them increasingly valuable to individuals and businesses. One of the issues with mobile devices that include cameras is that when multiple images of the same object are captured over time, it can be difficult to analyze changes in the objects because the images may not have been captured at the same distance or angle. Thus, changes in the objects that may appear to have occurred based upon the images may not have actually occurred.

SUMMARY

A mobile device includes a camera, a distance detection mechanism, a display, one or more processors, one or more memories communicatively coupled to the one or more processors, and an image acquisition application executing on the mobile device. The image acquisition application is configured to: cause a reference image of one or more objects to be displayed, on the display of the mobile device, as a background image in a manner that allows a user of the mobile device to simultaneously view one or more preview images of the one or more objects currently in a field of view of the camera. The image acquisition application is configured to cause the one or more preview images of the one or more objects currently in a field of view of the camera to be displayed simultaneously with the reference image on the display of the mobile device, cause the distance detection mechanism to detect a current distance between the camera and the one or more objects currently in the field of view of the camera, provide an indication to the user of the mobile device whether the current distance is within a specified amount of a distance at which the reference image was acquired, and in response to a user request to acquire an image, cause the camera to acquire a second image of the one or more objects.

BRIEF DESCRIPTION OF THE DRAWINGS

In the figures of the accompanying drawings like reference numerals refer to similar elements.

FIG. 2 is a flow diagram that depicts an approach for a mobile device to acquire images using a reference image as a background image and a distance at which the reference image was acquired.

FIG. 7A is a table that depicts an example patient database, where each row of the table corresponds to a patient and specifies an identifier, a date of birth (DOB), a gender, an ID list, a social security number (SSN), a sending facility, a family name, a first (given) name and another given (middle) name.

DETAILED DESCRIPTION

In the following description, for the purposes of explanation, numerous specific details are set forth in order to provide a thorough understanding of the embodiments. It will be apparent, however, to one skilled in the art that the embodiments may be practiced without these specific details. In other instances, well-known structures and devices are shown in block diagram form in order to avoid unnecessarily obscuring the embodiments.

I. OVERVIEW
II. SYSTEM ARCHITECTURE
  A. Mobile Device
  B. Application Server
III. ACQUIRING IMAGES USING A REFERENCE IMAGE AND DISTANCE
IV. MEMO AND AUDIO DATA
V. IMAGE DATA MANAGEMENT
VI. HISTORICAL VIEWS
VII. IMPLEMENTATION MECHANISMS I. Overview An approach is provided for acquiring and managing images. According to the approach, a reference image of one or more objects is displayed on the display of a mobile device in a manner that allows a user of the mobile device to simultaneously view the reference image and a preview image of the one or more objects currently in a field of view of a camera of the mobile device. For example, the reference image may be displayed on the display of the mobile device at a different brightness level, color, or with special effects, relative to the preview image. An indication is provided to the user of the mobile device whether the camera of the mobile device is currently located within a specified amount of a distance at which the reference image was acquired. For example, a visual or audible indication may indicate whether the camera of the mobile device is too close, too far away, or within a specified amount of a distance at which the reference image was acquired. In response to a user request to acquire an image, the camera acquires a second image of the one or more objects and a distance between the camera and the one or more objects at the time the second image was acquired is recorded. The second image and metadata are transmitted to an image management application that is external to the mobile device. For example, the second image and metadata may be transmitted over one or more networks to the image management application executing on an application server. The image management application provides various functionalities for managing images. For example, the image management application may allow a user to review and accept images, reject images and update metadata for images. As another example, the image management application provides a historical view that allows a user to view a sequence of images of one or more objects that were acquired at approximately the same distance and angle, which allows a user to better discern changes over time in the one or more objects.

II. System Architecture

Figure 1:
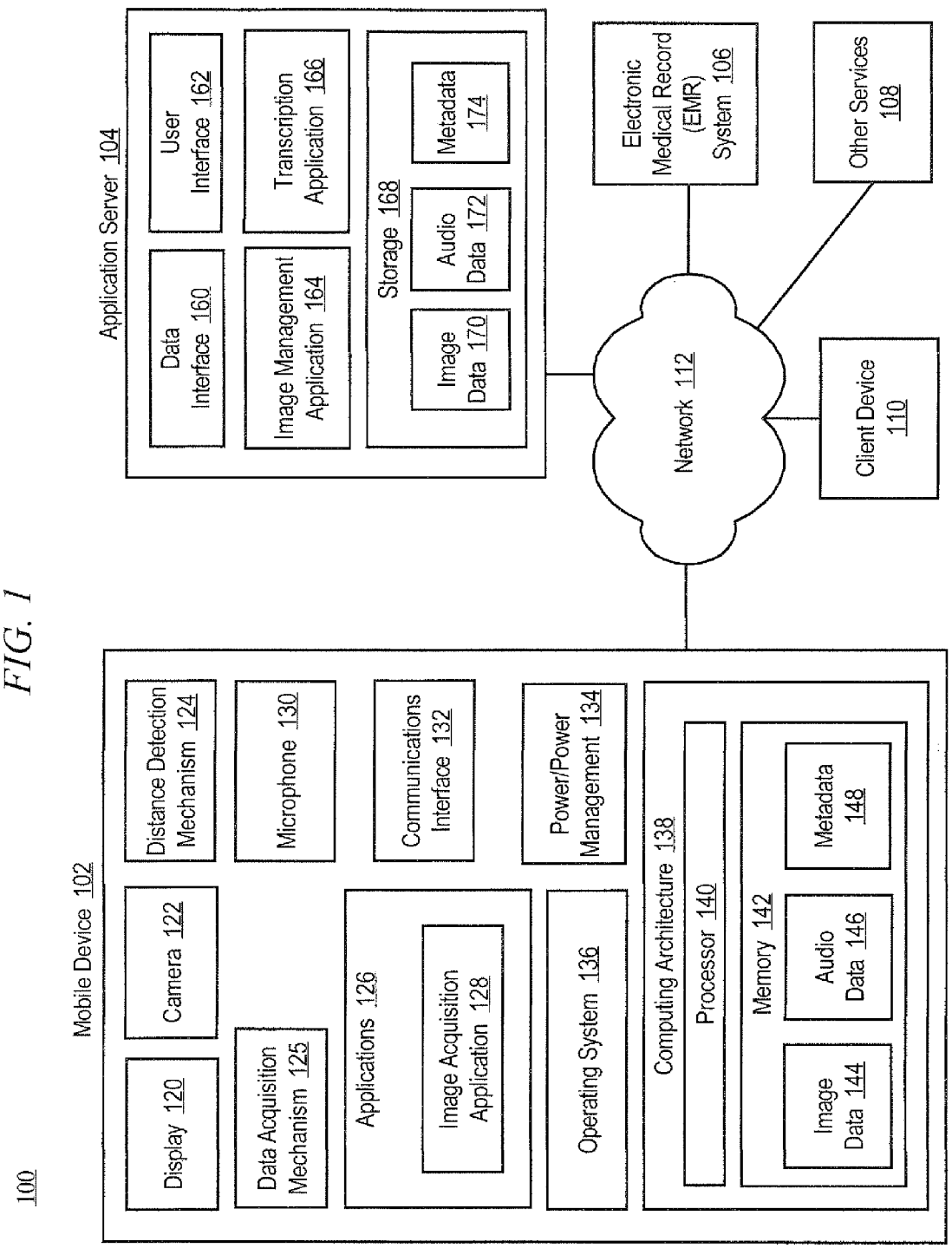
FIG. 1 is a block diagram that depicts an arrangement 100 for acquiring and managing images.

FIG. 1 is a block diagram that depicts an arrangement 100 for acquiring and managing images. Arrangement 100 includes a mobile device 102, an application server 104, an electronic medical record (EMR) system 106, other services 108 and a client device 110, communicatively coupled via a network 112. Arrangement 100 is not limited the particular elements depicted in FIG. 1 and may include fewer or additional elements depending upon a particular implementation. Embodiments are described herein in the context of a single mobile device 102 for purposes of explanation, but the approach is applicable to any number of mobile devices. Network 112 is depicted in FIG. 1 as a single network for purposes of explanation only and network 112 may include any number and type of wired or wireless networks, such as local area networks (LANs), wide area networks (WANs), the Internet, etc. The various elements depicted in FIG. 1 may also communicated with each other via direct communications links.

A. Mobile Device

Mobile device 102 may be any type of mobile device and examples of mobile device 102 include, without limitation, a smart phone, a camera, a tablet computing device, a personal digital assistant or a laptop computer. In the example depicted in FIG. 1, mobile device 102 includes a display 120, a camera 122, a distance detection mechanism 124, a data acquisition component 125, applications 126, including an image acquisition application 128, a microphone 130, a communications interface 132, a power/power management component 134, an operating system 136 and a computing architecture 138 that includes a processor 140 and memory 142, storing image data 144, audio data 146 and metadata 148. Mobile device 102 may include various other components that may vary depending upon a particular implementation and mobile device 102 is not limited to a particular set of components or features. For example, mobile device 102 may include a location component, such as one or more GPS components that is capable of determining a current location of mobile device 102 and generating location data that indicates the current location of mobile device 102. Mobile device 102 may also include manual controls, such as buttons, slides, etc., not depicted in FIG. 1, for performing various functions on mobile device, such as powering on/off or changing the state of mobile device 102 and/or display 120, or for acquiring digital images.

Display 120 may be implemented by any type of display that displays images and information to a user and may also be able to receive user input and embodiments are not limited to any particular implementation of display 120. Mobile device 102 may have any number of displays 102, of similar or varying types, located anywhere on mobile device 102. Camera 122 may be any type of camera and the type of camera may vary depending upon a particular implementation. As with display 120, mobile device 102 may be configured with any number of cameras 104 of similar or varying types, for example, on a front and rear surface of mobile device 102, but embodiments are not limited to any number or type of camera 122.

Distance detection mechanism 124 is configured to detect a distance between the camera 122 on mobile device 102 and one or more objects within the field of view of the camera 122. Example implementations of distance detection mechanism may be based upon, without limitation, infra-red, laser, radar, or other technologies that use electromagnetic radiation. Distance may be determined directly using the distance detection mechanism 124, or distance may be determined from image data. For example, the distance from the camera 122 to one or more objects on the ground and in the field of view of the camera 122 may be calculated based upon a height of the camera 122 and a current angle of the camera 122 with respect to the ground. For example, given a height (h) of the camera 122 and an acute angle (a) between the vertical and a line of sight to the one or more objects, the distance (d) may be calculated as follows: $d=h*\tan(a)$. As another example, if one or more dimensions of the one or more objects are known, the distance between the camera 122 and the one or more objects may be determined based upon a pixel analysis of the one or more objects for which the one or more dimensions are known.

Data acquisition component 125 may comprise hardware subcomponents, programmable subcomponents, or both. For example, data acquisition component 125 may include one or more cameras, scanners, memory units or other data storage units, buffers and code instructions for acquiring, storing and transmitting data, or any combination thereof.

Data acquisition component 125 may be configured with a Wi-Fi interface and a barcode reader. The Wi-Fi interface may be used to transmit information to and from the data acquisition component 125. The barcode reader may be used to scan or otherwise acquire a code, such as a point of sale (POS) code displayed on an item.

Microphone 130 is configured to detect audio and in combination with other elements, may store audio data that represents audio detected by microphone 130. Communications interface 132 may include computer hardware, software, or any combination of computer hardware and software to provide wired and/or wireless communications links between mobile device 102 and other devices and/or networks. The particular components for communications interface 132 may vary depending upon a particular implementation and embodiments are not limited to any particular implementation of communications interface 132. Power/power management component 134 may include any number of components that provide and manage power for mobile device 102. For example, power/power management component 134 may include one or more batteries and supporting computer hardware and/or software to provide and manage power for mobile device 102.

Computing architecture 138 may include various elements that may vary depending upon a particular implementation and mobile device 102 is not limited to any particular computing architecture 138. In the example depicted in FIG. 1, computing architecture includes a processor 108 and a memory 142. Processor 108 may be any number and types of processors and memory 142 may be any number and types of memories, including volatile memory and non-volatile memory, which may vary depending upon a particular implementation. Computing architecture 138 may include additional hardware, firmware and software elements that may vary depending upon a particular implementation. In the example depicted in FIG. 1 memory 142 stores image data 144, audio data 146 and metadata 148, as described in more detail hereinafter, but memory 142 may store additional data depending upon a particular implementation.

Operating system 136 executes on computing architecture 138 and may be any type of operating system that may vary depending upon a particular implementation and embodiments are not limited to any particular implementation of operating system 136. Operating system 136 may include multiple operating systems of varying types, depending upon a particular implementation. Applications 126 may be any number and types of applications that execute on computing architecture 138 and operating system 136. Applications 126 may access components in mobile device 102, such as display 120, camera 122, distance detection mechanism 124, computing architecture 138, microphone 130, communications interface 132, power/power management component 134 and other components not depicted in FIG. 1, via one or more application program interfaces (APIs) for operating system 136.

Applications 126 may provide various functionalities that may vary depending upon a particular application and embodiments are not limited to applications 126 providing any particular functionality. Common non-limiting examples of applications 126 include social media applications, navigation applications, telephony, email and messaging applications, and Web service applications. In the example depicted in FIG. 1, applications 126 include an image acquisition application 128 that provides various functionalities for acquiring images. Example functionality includes allowing a user to acquire images via camera 122 while a reference image is displayed as a background image. In this example, the image acquisition application 128 is also configured to provide an indication to a user, e.g., a visual or audible indication, to indicate whether the camera 122 of the mobile device 102 is too close, too far away, or within a specified amount of a distance at which the reference image was acquired. Other example functionality includes acquiring metadata, memorandum data and/or audio data that corresponds to the acquired images, and transmitting this information with the acquired images to an image management application that is external to the mobile device 102. These and other example functionalities of image acquisition application 128 are described in more detail hereinafter. Image acquisition application 128 may be implemented in computer hardware, computer software, or any combination of computer hardware and software.

B. Application Server

In the example depicted in FIG. 1, application server 104 includes a data receiver 160, a user interface 162, an image management application 164, a transcription application 166 and storage 168 that includes image data 170, audio data 172 and metadata 174. Application server 104 may include various other components that may vary depending upon a particular implementation and application server 104 is not limited to a particular set of components or features. Application server 104 may include various hardware and software components that may vary depending upon a particular implementation and application server 104 is not limited to any particular hardware and software components.

Data receiver 160 is configured to receive data from mobile device 102 and may do so using various communication protocols and from various media. Example protocols include, without limitation, the File Transfer Protocol (FTP), the Telnet Protocol, the Transmission Control Protocol (TCP), the TCP/Internet Protocol (TCP/IP), the Hypertext Transfer Protocol (HTTP), the Simple Mail Transfer Protocol (SMTP), or any other data communications protocol. Data receiver 118 may be configured to read data from an FTP folder, an email folder, a Web server, a remote media such as a memory stick, or any other media. Data receiver 160 may include corresponding elements to support these transport methods. For example, data receiver 160 may include, or interact with, an FTP server that processes requests from an FTP client on mobile device 102. As another example, data receiver 160 may include, or interact with, an email client for retrieving emails from an email server on mobile device 102 or external to mobile device 102. As yet another example, data receiver 160 may include, or interact with, a Web server that responds to requests from an http client on mobile device 102. Data interface 160 is further configured to support the transmission of data from application server 104 to other devices and processes, for example, EMR system 106, other services 108 and client device 110.

User interface 160 provides a mechanism for a user, such as an administrator, to access application server 104 and data stored on storage 168, as described in more detail hereinafter. User interface 160 may be implemented as an API for application server 104. Alternatively, user interface 160 may be implemented by other mechanisms. For example, user interface 160 may be implemented as a Web server that serves Web pages to provide a user interface for application server 104.

Image management application 164 provides functionality for managing images received from mobile device 102 and stored in storage 168. Example functionality includes reviewing images, accepting images, rejecting images, processing images, for example to improve blurriness or otherwise enhance the quality of images, crop or rotate images, etc., as well as update metadata for images. Example functionality also includes providing a historical view of a sequence of images of one or more objects, where the images in the sequence were acquired using a reference image as a background image and at approximately the same distance from the one or more objects. According to one embodiment, image management application 164 provides a graphical user interface to allow user access to the aforementioned functionality. The graphical user interface may be provided by application software on client device 110, application software on application server 104, or any combination of application software on client device 110 and application server 104. As one example, the graphical user interface may be implemented by one or more Web pages generated on application server 104 and provided to client device 110. Image management application 164 may be implemented in computer hardware, computer software, or any combination of computer hardware and software. For example, image management application 164 may be implemented as an application, e.g., a Web application, executing on application server 104.

Transcription application 166 processes audio data acquired by mobile device 102 and generates a textual transcription. The textual transcription may be represented by data in any format that may vary depending upon a particular implementation. Storage 168 may include any type of storage, such as volatile memory and/or non-volatile memory. Data transmitter 122 is configured to provide image and/or video data and identification data to auto insurance system 106, EMR system 108 and other services 110. Data transmitter 122 transmits the data to auto insurance system 106, EMR system 106 and other services 108 using standard techniques or alternatively, data transmitter 122 may transmit data to auto insurance system 106, EMR system 108 and other services 110 in accordance with Application Program Interfaces (APIs) supported by auto insurance system 106, EMR system 108 and other services 110. Application server 104 may be implemented as a stand-alone network element, such as a server or intermediary device. Application server 104 may also be implemented on a client device, including mobile device 102.

III. Acquiring Images Using a Reference Image and Distance

According to one embodiment, mobile device 102 is configured to acquire image data using a reference image as a background image and a distance at which the reference image was acquired.

Figure 3A:
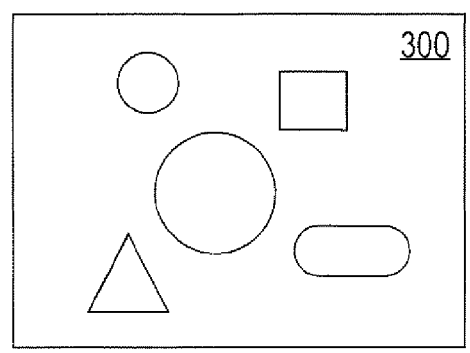
FIG. 3A depicts an example reference image that includes one or more objects that are represented by different shapes.

FIG. 2 is a flow diagram 200 that depicts an approach for a mobile device to acquire images using a reference image as a background image and a distance at which the reference image was acquired, according to an embodiment. In step 202, a reference image to be used as a reference image is retrieved. The reference image may be retrieved in response to a user invoking the image acquisition application 128 and specifying an image to be used as the reference image. For example, a user may select an icon on display 120 that corresponds to the image acquisition application 128 to invoke the image acquisition application 128 and the user is then queried for an image to be used as a reference image. The user may then select an image to be used as the reference image, or specify a location, e.g., a path, of an image to be used as the reference image. The reference image may originate and be retrieved from any source. For example, the reference image may have been acquired by mobile device 102 via camera 122 and be stored as image data 144 in memory 142, or at a location external to mobile device 102. As another example, the reference image may have been acquired by a device external to mobile device, such as client device 110, a scanner, or other services 108. The reference image data may be any type or format of image data. Example image data formats include, without limitation, raster formats such as JPEG, Exif, TIFF, RAW, GIF, BMP, PNG, PPM, PGM, PBM, PNM, etc., and vector formats such as CGM, SVG, etc. The reference image may have corresponding metadata 148 that describes one or more attributes of the reference image. Example attributes include, without limitation, camera settings used to acquire the reference image, and a distance from the camera used to acquire the reference image to the one or more objects in the reference image. FIG. 3A depicts an example reference image 300 that includes one or more objects that are represented by different shapes.

Figure 3B:
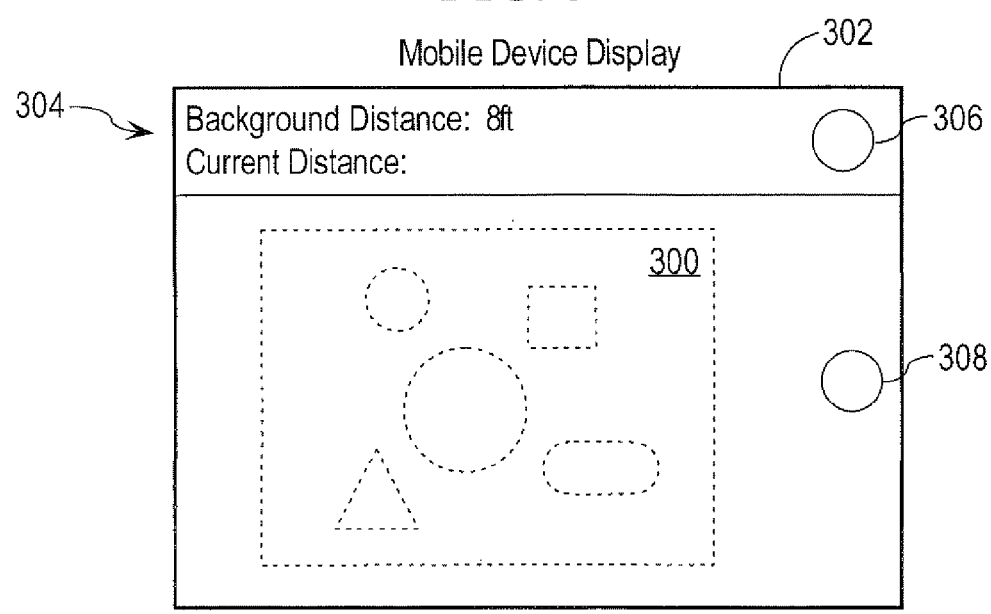
FIG. 3B depicts a distance at which a reference image was acquired.

In step 204, the reference image is displayed on the mobile device as a background image. For example, image acquisition application 128 may cause the reference image to be displayed on display 120 of mobile device 102. FIG. 3B depicts an example mobile device display 302 that may be, for example, display 120 of mobile device 102. In this example, the reference image 300, which includes the one or more objects, is displayed on the mobile device display 302 as a background image in a manner that allows a user of the mobile device to simultaneously view a preview image of the one or more objects currently in a field of view of the camera. This may be accomplished using a wide variety of techniques that may vary depending upon a particular implementation and embodiments are not limited to any particular technique for displaying the reference image as a background image. For example, one or more attribute values for the reference image 300 may be changed. The attribute values may correspond to one or more attributes that affect the way in which the reference image appears on the mobile device display to a user. Example attributes include, without limitation, brightness, color or special effects. The reference image 300 may be displayed on mobile device display 302 using a lower brightness or intensity than would normally be used to display images on mobile device display 302. As another example, the reference image 300 may be displayed using a different color, shading, outline, or any other visual effect that visually identifies the reference image 300 to a user as a background image.

According to one embodiment, a distance at which the reference image was acquired is indicated on the display of the mobile device. For example, as depicted in FIG. 3B, the distance at which the reference image was acquired may be displayed on the mobile device display 302 by "Background distance: 8 ft", as indicated by reference numeral 304. In this example, the "Current Distance" is the current distance between the mobile device 102 and the one or more objects currently in the field of view of the camera and viewable by a user as a preview image, as described in more detail hereinafter. The background distance and/or the current distance may be indicated by other means that may vary depending upon a particular implementation, and embodiments are not limited to any particular means for indicating the background distance and the current distance. For example, the background distance and current distance may be indicated by symbols, colors, shading and other visual effects on mobile device display 302.

Figure 3C:
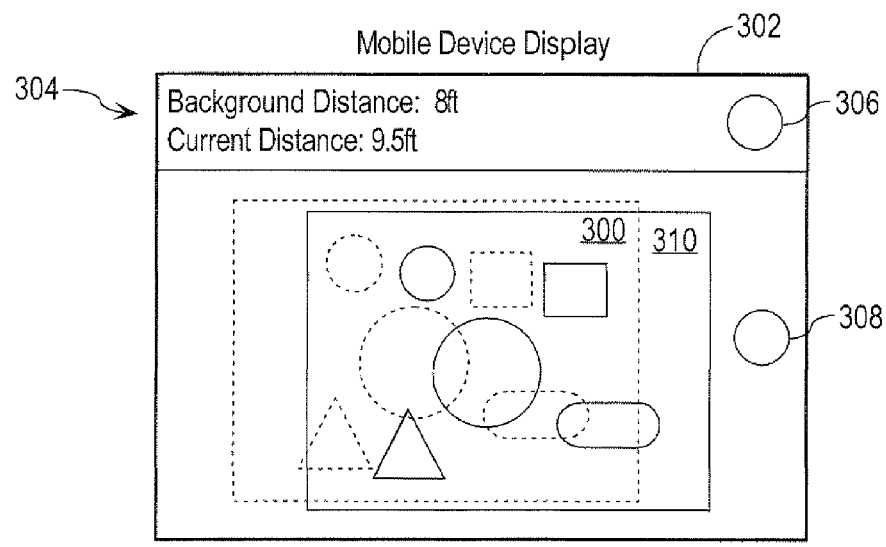
In FIG. 3C, a preview image is displayed on a mobile device display
Figure 3D:
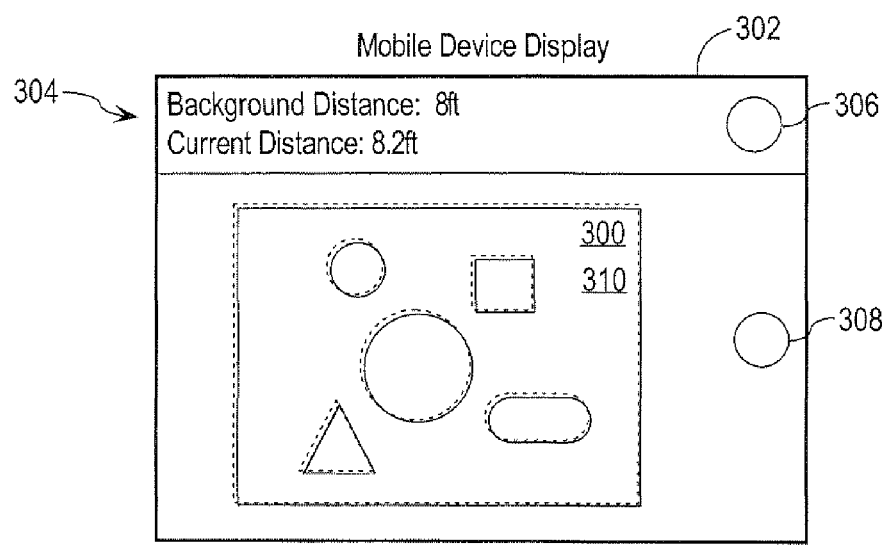
FIG. 3D depicts a mobile device that has been positioned and oriented so that the one or more objects in a reference image and one or more preview images overlap

In step 206, one or more preview images are displayed of one or more objects currently in the field of view of the camera. For example, image acquisition application 128 may cause one or more preview images to be acquired and displayed on display 120. In FIG. 3C, a preview image 310 is displayed on the mobile device display 302. Embodiments are described herein in the context of displaying a single preview image 310 for purposes of explanation only and multiple preview images may be displayed, as described in more detail hereafter. According to one embodiment, the preview image 310 is displayed in a manner to be visually discernable by a user from the reference image 300 displayed as a background image. For example, the preview image 310 may be displayed on the mobile device display 302 using normal intensity, brightness, color, shading, outline, other special effects, etc. Displaying the preview image 310 simultaneously with the reference image 300 displayed as a background image allows a user to visually discern any differences between the distance, height and angle at which the reference image was acquired and the distance, height and angle of the preview image currently displayed on the mobile device display 302. For example, differences in distance may be readily discerned from differences in sizes of the one or more objects, represented in FIG. 3C by the triangle, rectangle, oval and circles in both the reference image 300 and the preview image 310. Differences in angle may be readily discerned when the one or more objects in the reference image 300 and the preview image 310 are three dimensional objects. This allows a user to move and/or orient the mobile device 102 so that the one or more objects depicted in the preview image 310 overlap, or are aligned with, the one or more objects depicted in the reference image 300. Furthermore, successive preview images 310 may be displayed on mobile device display 302, for example on a continuous basis, to allow a user to move and/or reorient the mobile device 102 so that the distance, height and angle of the one or more objects in the reference image 300 and the one or more preview images 310 are at least substantially the same. For example, as depicted in FIG. 3D, the mobile device 102 has been positioned and oriented so that the one or more objects in the reference image 300 and the one or more preview images overlap, indicating that the distance, height and angle of the one or more objects in the reference image 300 and the one or more preview images 310 are at least substantially the same.

In step 208, a determination is made of a current distance between the mobile device and the one or more objects currently in the field of view of the camera. For example, image acquisition application 128 may cause the distance detection mechanism to measure a current distance between the mobile device 102 and the one or more objects in the field of view of the camera 122. As another example, a current distance between the mobile device 102 and the one or more objects in the field of view of the camera 122 may be determined using a GPS component in mobile device 102 and a known location of the one or more objects. In this example, the GPS coordinates of the mobile device 102 may be compared to the GPS coordinates of the one or more objects to determine the current distance between the mobile device 102 and the one or more objects in the field of view of the camera 122.

In step 210, an indication is provided to a user of the mobile device whether the current distance is within a specified amount of the distance at which the reference image was acquired. For example, the image acquisition application 128 may compare the current distance between the mobile device 102 and the one or more objects, as determined in step 208, to the distance at which the reference image was acquired. The result of this comparison may be indicated to a user of the mobile device 102 in a wide variety of ways that may vary depending upon a particular implementation and embodiments are not limited to any particular manner of notification. For example, the image acquisition application 128 may visually indicate on the display 120 whether the current distance is within a specified amount of the distance at which the reference image was acquired. This may include, for example, displaying one or more icons on display 120 and/or changing one or more visual attributes of icons displayed on display 120. As one example, icon 306 may be displayed in red when the current distance is not within the specified amount of the distance at which the reference image was acquired, displayed in yellow when the current distance is close to being within the specified amount of the distance at which the reference image was acquired and displayed in green when the current distance is within the specified amount of the distance at which the reference image was acquired. As another example, an icon, such as a circle may be displayed and the diameter reduced as the current distance approaches the specified amount of the distance at which the reference image was acquired. The diameter of the circle may increase as the difference between the current distance and distance at which the reference image was acquired increases, indicating that the mobile device 102 is getting farther away from the distance at which the reference image was acquired. As another example, different icons or symbols may be displayed to indicate whether the current distance is within the specified amount of the distance at which the reference image was acquired. As one example, a rectangle may be displayed when the mobile device 102 is beyond a specified distance from the distance at which the reference image was acquired and then changed to a circle as the mobile device 102 approaches the distance at which the reference image was acquired.

Image acquisition application 128 may audibly indicate whether the current distance is within a specified amount of the distance at which the reference image was acquired, for example, by generating different sounds. As one example, the mobile device 102 may generate a sequence of sounds, and the amount of time between each sound is decreased as the mobile device approaches the distance at which the reference image was acquired. The current distance between the mobile device 102 and the one or more objects in the field of view of the camera 122 may also be displayed on the display, for example, as depicted in FIGS. 3C and 3D. In this example, the current distance has changed from 9.5 ft to 8.2 ft as the user moved and/or reoriented the mobile device 102, to be closer to the 8.0 ft at which the reference image was acquired.

In step 212, a second image of the one or more objects is acquired in response to a user request. For example, in response to a user selection of a button 308, the second image of the one or more objects that are currently in the field of view is acquired. Metadata is also generated for the second image and may specify, for example, camera parameter values used to acquire the second image, and a timestamp or other data, such as a sequence identifier, that indicates a sequence in which images were acquired. According to one embodiment, the metadata for the second image includes a reference to the reference image so that the reference image and the second image can be displayed together, as described in more detail hereinafter. The reference may be in any form and may vary depending upon a particular implementation. For example, the reference may include the name or identifier of the reference image. The metadata for the reference image may also be updated to include a reference to the second image.

According to one embodiment, camera settings values used to acquire the reference image are also used to acquire the second image. This ensures, for example, that the same camera settings, such as focus, aperture, exposure time, etc., are used to acquire both the reference image and the second image. This reduces the likelihood that differences in the one or more objects in the sequence of images are attributable to different camera settings used to acquire the images, rather than actual changes in the one or more objects. Camera settings used to acquire an image may be stored in the metadata for the acquired image, for example, in metadata 148, 174.

The current distance may optionally be reacquired and recorded in association with the second image, for example, in the metadata for the second image. Alternatively, the distance at which the reference image was acquired may be used for the second image, since the current distance is within the specified amount of the distance at which the reference image was acquired.

Image data, representing the second image, and optionally the current distance, may be stored locally on mobile device, for example, in memory 142, and/or may be transmitted by mobile device 102 for storage and/or processing on one or more of application server 104, EMR system 106, other services 108 or client device 110. Image data may be transmitted to application server 104, EMR system 106, other services 108 or client device 110 using a wide variety of techniques, for example, via FTP, via email, via http POST commands, or other approaches. The transmission of image data, and the corresponding metadata, may involve the verification of credentials. For example, a user may be queried for credential information that is verified before image data may be transmitted to application server 104, EMR system 106, other services 108 or client device 110. Although the foregoing example is depicted in FIG. 2 and described in the context of acquiring a second image, embodiments are not limited to acquiring a single image using a reference image and any number of subsequent images may be acquired using a reference image as a background image. When more than one subsequent images are acquired using a reference image, the metadata for the subsequent images may include a reference to the reference image and the other subsequent images that were acquired using the reference image. For example, suppose that a second and third image were acquired using the reference image. The metadata for the second image may include a reference to the reference image and to the third image. The metadata for the third image may include a reference to the reference image and the second image. The metadata for the reference image may include no references the second and third images, a reference to the second image, a reference to the third image, or both. The reference data and timestamp data are used to display the reference image and one or more subsequent images acquired using the reference image as a background image as an ordered sequence, as described in more detail hereinafter.

IV. Memo and Audio Data

According to one embodiment, memorandum (memo) and/or audio data may be acquired to supplement image data. Memorandum data may be automatically acquired by data acquisition component 125, for example, by scanning encoded data associated with the one or more objects in the acquired image. For example, a user of mobile device 102 may scan a bar code or QR code attached to or otherwise associated with the one or more objects, or by scanning a bar code or QR code associated with a patient, e.g., via a patient bracelet or a patient identification card. Memorandum data may be manually specified by a user of mobile device 102, for example, by selecting from one or more specified options, e.g., via pull-down menus or lists, or by entering alphanumeric characters and/or character strings.

Figure 4B:
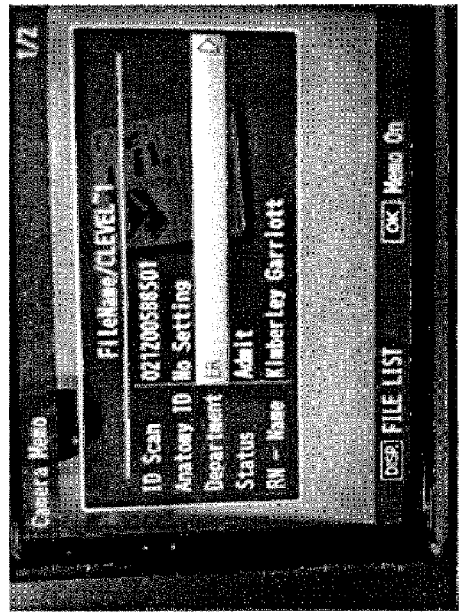
FIG. 4B depicts that a user has used one or more controls (graphical or physical) on a mobile device to navigate to the department field.
Figure 4D:
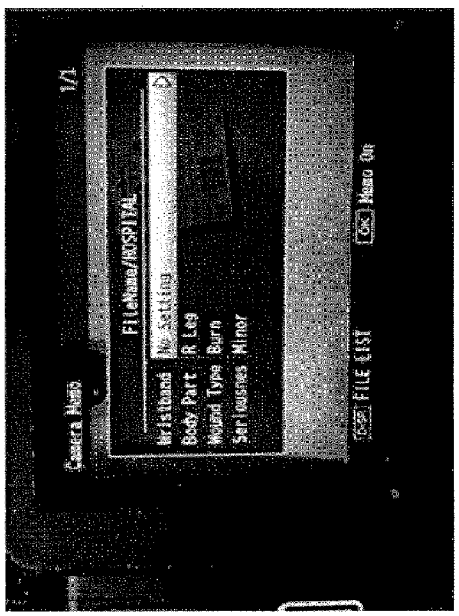
FIG. 4D depicts a graphical user interface allows the user to specify a wristband setting, a body part, a wound type and an indication of the seriousness of the injury.
Figure 4A:
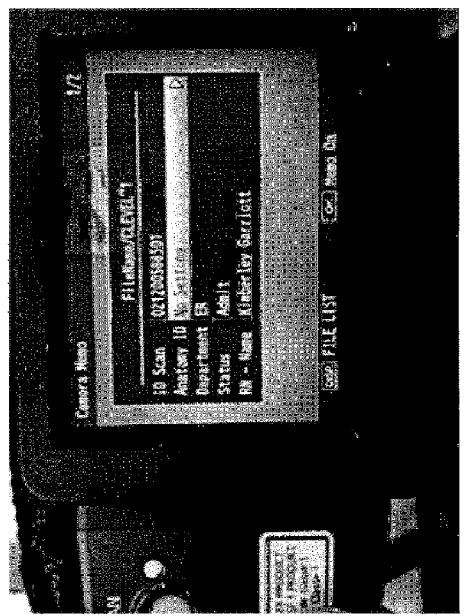
FIG. 4A depicts top-level information that includes a patient identification field ("ID Scan"), an anatomy identification field ("Anatomy ID"), a department field ("Department"), a status field ("Status") and a registered nurse name ("RN-Name").
Figure 4C:
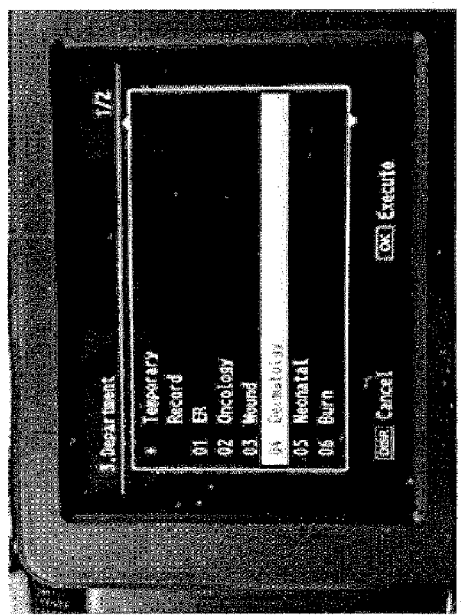
FIG. 4C depicts the department options available to the user after selecting the department field and that the user has navigated to the Dermatology department option.

FIGS. 4A-D depict an example graphical user interface displayed on display 120 of mobile device 102 that allows a user to specify memorandum data in a medical context. The graphical user interface may be generated, for example, by image acquisition application 128. FIG. 4A depicts top-level information that includes a patient identification field ("ID Scan"), an anatomy identification field ("Anatomy ID"), a department field ("Department"), a status field ("Status") and a registered nurse name ("RN-Name"). FIG. 4B depicts that a user has used one or more controls (graphical or physical) on mobile device 102 to navigate to the department field. FIG. 4C depicts the department options available to the user after selecting the department field and that the user has navigated to the Dermatology department option. In FIG. 4D, the graphical user interface allows the user to specify a wristband setting, a body part, a wound type and an indication of the seriousness of the injury.

Figure 5A:
FIG. 5A depicts a table of example types of memorandum data.

FIG. 5A depicts a table 500 of example types of memorandum data. Although embodiments are described in the context of example types of memorandum data for purposes of explanation, embodiments are not limited to any particular types of memorandum data. In the example table 500 depicted in FIG. 5A, the memorandum data is in the context of images of a human wound site and includes a patient ID, an employee ID, a wound location, an anatomy ID, a wound distance, i.e., a distance between the camera 122 and the wound site, a date, a department, a doctor ID and a status.

Audio data may be acquired, for example, by image acquisition application 128 invoking functionality provided by operating system 136 and/or other applications 126 and microphone 130. The acquisition of audio data may be initiated by user selection of a graphical user interface control or other control on mobile device 102. For example, a user may initiate the acquisition of audio data at or around the time of acquiring one or more images to supplement the one or more images. As described in more detail hereinafter, audio data may be processed by transcription application 166 to provide an alphanumeric representation of the audio data.

Memorandum data and/or audio data may be stored locally on mobile device, for example, in memory 142, and/or may be transmitted by mobile device 102 for storage and/or processing on one or more of application server 104, EMR system 106, other services 108 or client device 110. Memorandum data may be stored as part of metadata 148, 174. Audio data may be stored locally on mobile device 102 as audio data 146 and on application server 104 as audio data 172. In addition, memorandum data and/or audio data may be transmitted separate from or with image data, e.g., as an attachment, embedded, etc.

Figure 5B:
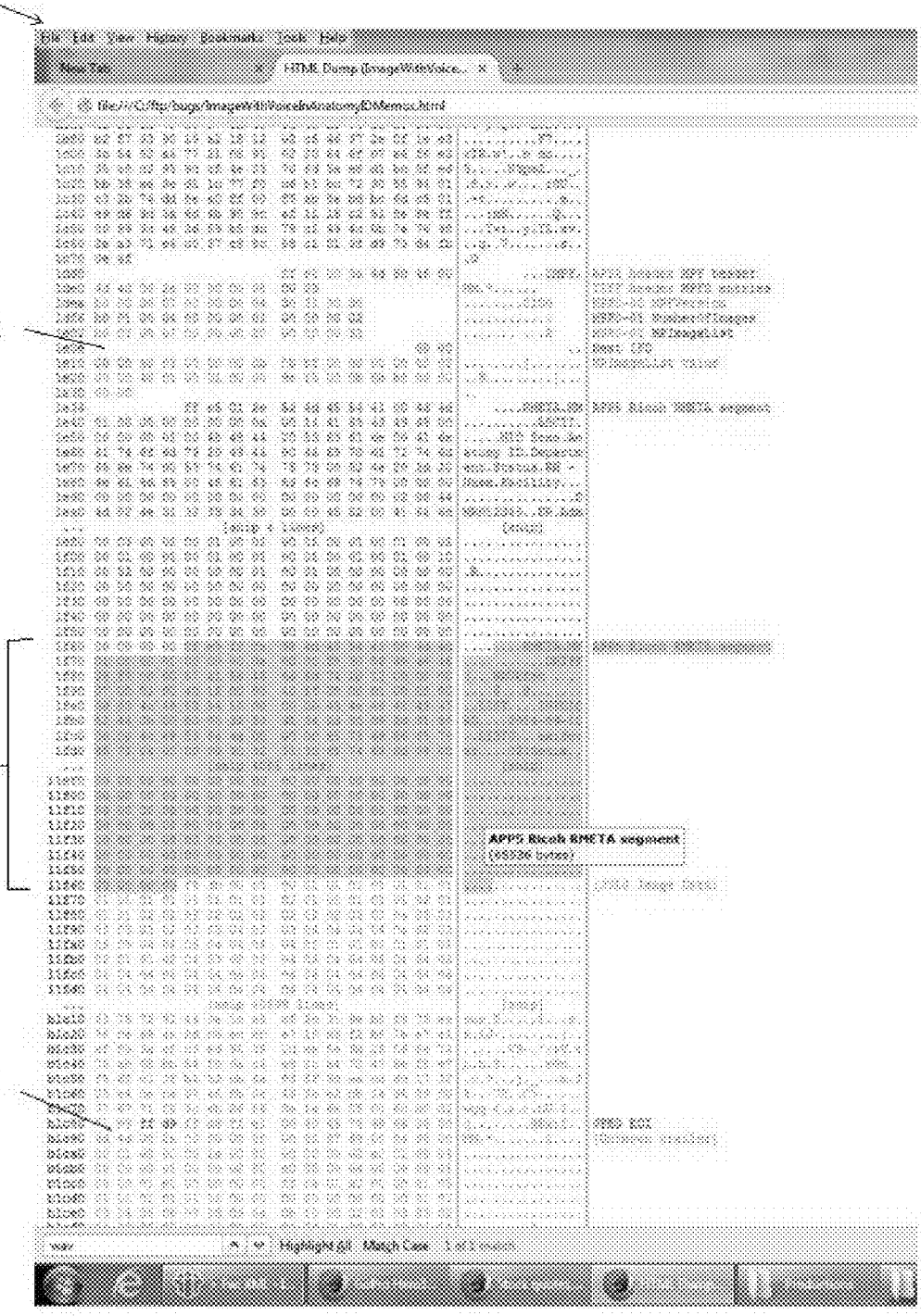
FIG. 5B is a table that depicts a textual representation of image data 552 that includes embedded audio data.

FIG. 5B is a table 550 that depicts a textual representation of image data 552 that includes embedded audio data 554. In this example, audio data 146, 172 is stored as part of image data 144, 170. Memorandum data may similarly be embedded in image data. The way in which memorandum data and audio data is stored may vary from image data to image data and not all memorandum data and audio data must be stored in the same manner. For example, audio data that corresponds to a reference image may be embedded in the image data for the reference image, while audio data that corresponds to a second image may be stored separate from the image data for the second image.

V. Image Data Management

Various approaches are provided for managing image data. According to one embodiment, image management application 164 provides a user interface for managing image data. The user interface may be implemented, for example, as a Web-based user interface. In this example, a client device, such as client device 110, accesses image management application 164 and the user interface is implemented by one or more Web pages provided by image management application 164 to client device 110.

Figure 6A:
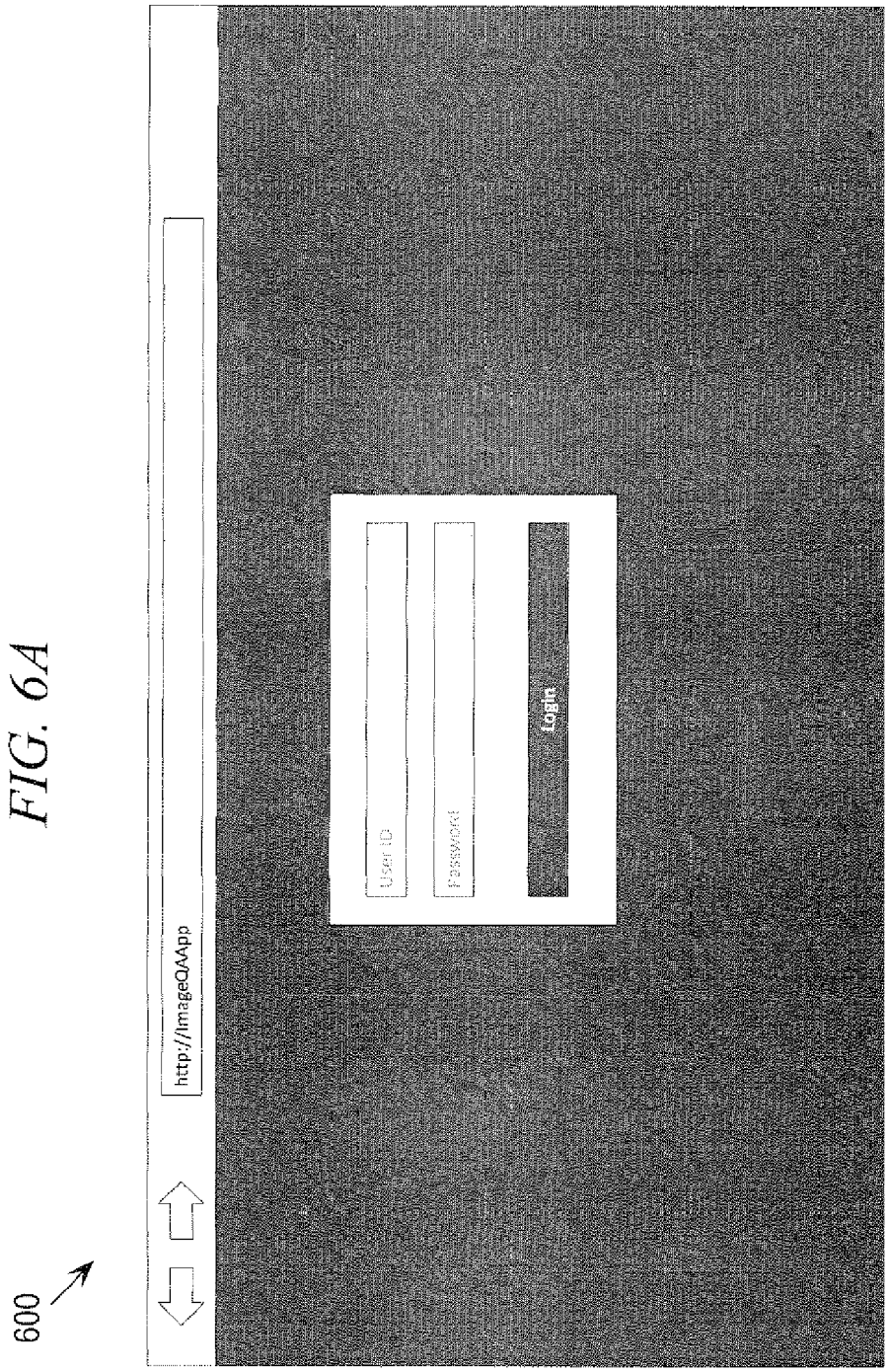
FIG. 6A depicts an example login screen that queries a user for user credentials that include a user login ID and password.

FIGS. 6A-6D depict an example graphical user interface for managing image data according to an embodiment. The example graphical user interface depicted in FIGS. 6A-6D may be provided by one or more Web pages generated on application server 104 and provided to client device 110. FIG. 6A depicts an example login screen 600 that queries a user for user credentials that include a user login ID and password.

Figure 6B:
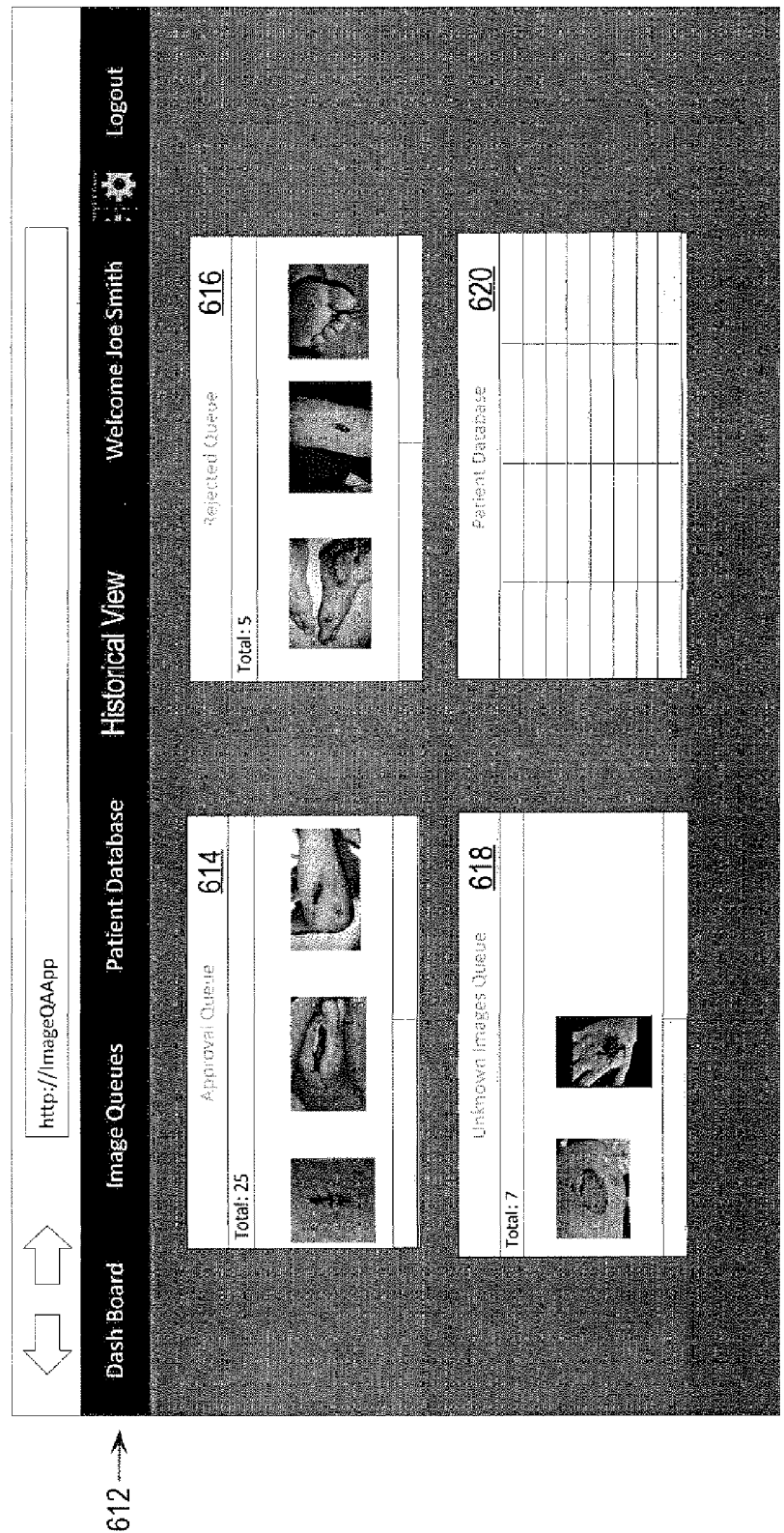
FIG. 6B depicts an example dashboard screen that provides access to various functionality for managing image data.

FIG. 6B depicts an example main screen 610, referred to hereinafter as a "dashboard 610", that provides access to various functionality for managing image data. In the example depicted in FIG. 6B, the dashboard 610 provides access, via graphical user interface controls 612, to logical collections of images referred to hereinafter as "queues," a user database in the form of a patient database and historical views of images. Although embodiments are described hereinafter in the medical/accident context for purposes of explanation, embodiments are not limited to this context. The queues include an Approval Queue, a Rejected Queue and an Unknown Images Queue that may be accessed via graphical user interface icons 614, 616, 618, respectively. The patient database may be accessed via graphical user interface icon 620.

Figure 6C:
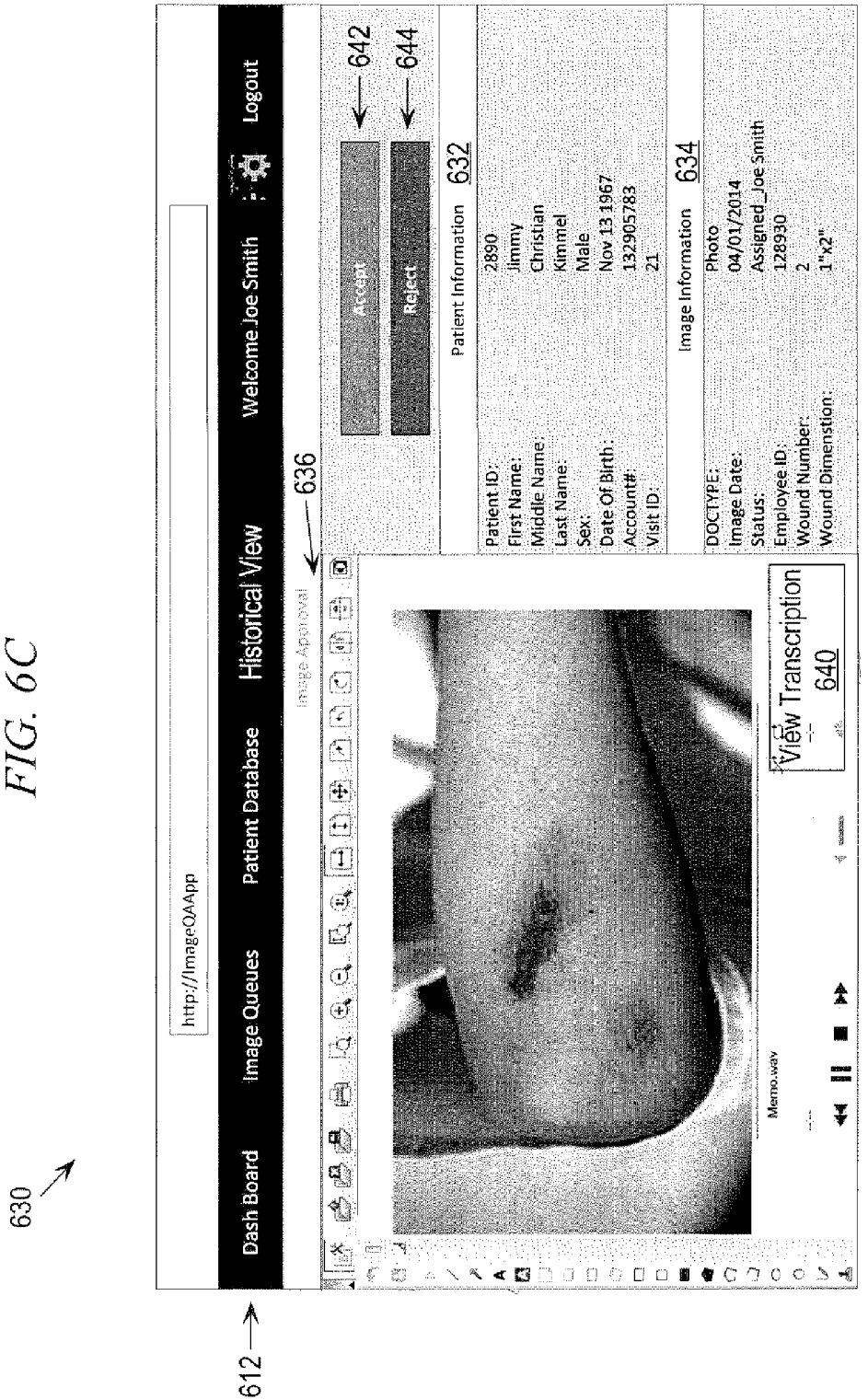
FIG. 6C depicts an example Approval Queue screen, or work queue, that allows a user to view and approve or reject images.

FIG. 6C depicts an example Approval Queue screen 630, or work queue, that allows a user to view and approve or reject images. Approval Queue screen 630 displays patient information 632 of a patient that corresponds to the displayed image and image information 634 for the displayed image. Approval Queue screen 630 includes controls 636 for managing the displayed image, for example, by expanding (horizontally or vertically) or rotating the displayed image. Controls 638 allow a user to play an audio recording that corresponds to the displayed image. Control 640 allows a user to view an alphanumeric transcription of the audio recording that corresponds to the displayed image. The alphanumeric transcription may be generated by transcription application 166 and displayed to a user in response to a user selection of control 640. Approval Queue screen 630 also includes controls 640, 642 for approving (accepting) or rejecting, respectively, the displayed image. A displayed image might be rejected for a wide variety of reasons that may vary depending upon a particular situation. For example, a user might choose to reject a displayed image because the image is out of focus, the image is otherwise of poor quality, the image does not show the area of interest, or the information associated with the image, such as the patient information 632 or the image information 634 is incomplete.

Figure 6D:
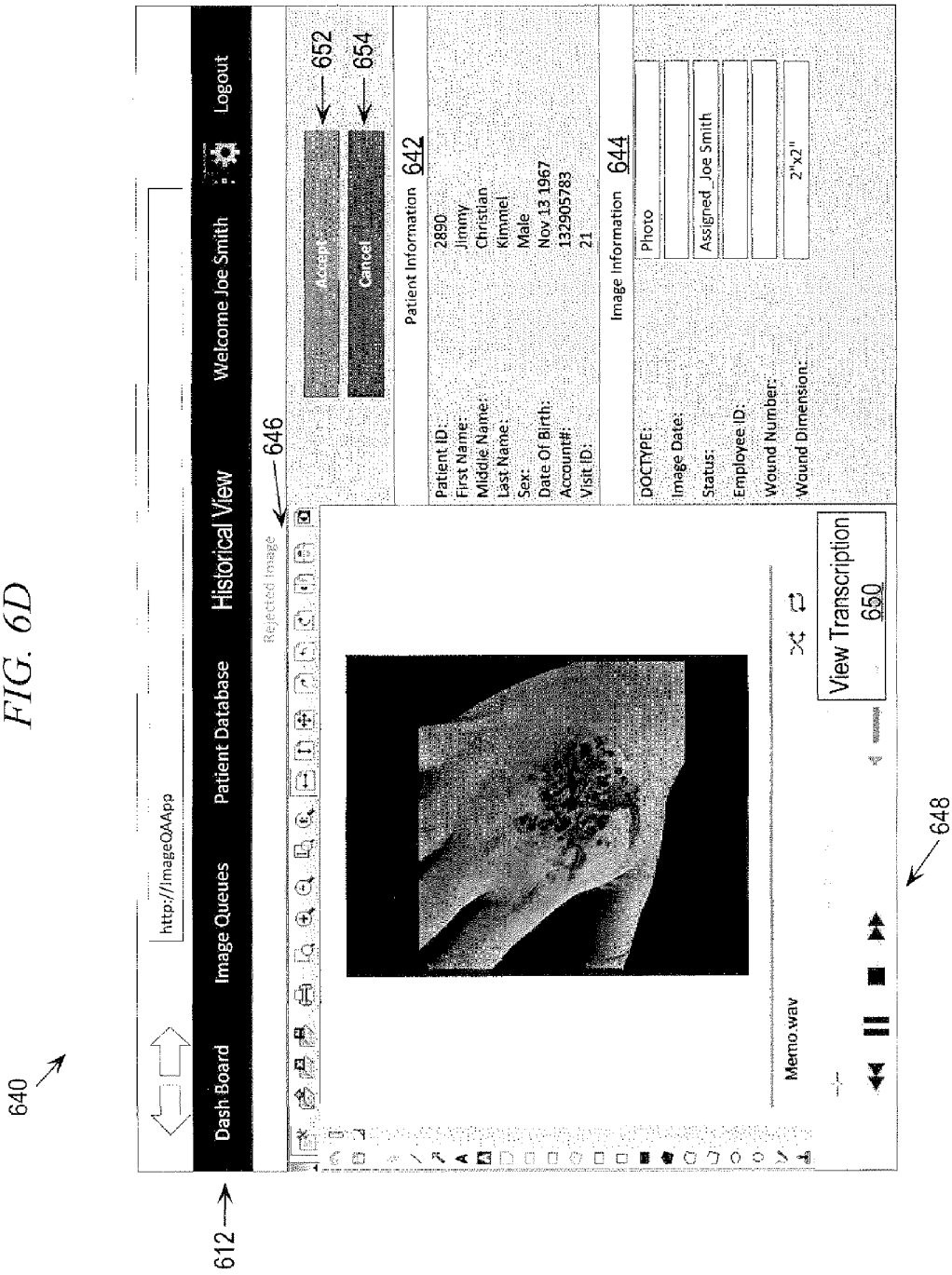
FIG. 6D depicts an example Rejected Image Processing screen that allows a user to view and update information for rejected images.

FIG. 6D depicts an example Rejected Image Processing screen 640 that allows a user to view and update information for rejected images. Rejected Image Processing screen 640 displays patient information 642 of a patient that corresponds to the displayed image and image information 644 for the displayed image. A user may correct or add to the meta data or memorandum data for the displayed image. For example, the user may correct or add to the patient information 642 or the image information 644, e.g., by selecting on a field and manually entering alphanumeric information. Rejected Image Processing screen 640 includes controls 646 for managing the displayed image, for example, by expanding (horizontally or vertically) or rotating the displayed image. Controls 648 allow a user to play an audio recording that corresponds to the displayed image. Control 650 allows a user to view an alphanumeric transcription of the audio recording that corresponds to the displayed image. Rejected Image Processing screen 640 also includes controls 640, 642 for approving (accepting) or rejecting, respectively, the displayed image. For example, after making changes to the displayed image, the patient information 642 or the image information 644, a user may select control 652 to accept the displayed image and cause the displayed image to be added to the Approval queue. Alternatively, a user may maintain the displayed image as rejected by selecting control 654 to cancel.

The unknown images queue accessed via control 618 includes images for which there are incomplete information or other problems, which may occur for a variety of reasons. For example, a particular image may have insufficient metadata to associate the particular image with other images. As another example, a particular image may be determined to not satisfy specified quality criteria, such as sharpness, brightness, etc. Users may perform processing on images in the unknown images queue to provide incomplete information and/or address problems with the images. For example, a user may edit the metadata for a particular image in the unknown images queue to supply missing data for the particular image. As another example, a user may process images in the unknown image queue to address quality issues, such as poor focus, insufficient brightness or color contrast, etc. The images may then be approved and moved to the approval queue or rejected and moved to the rejected queue.

Figure 7A:
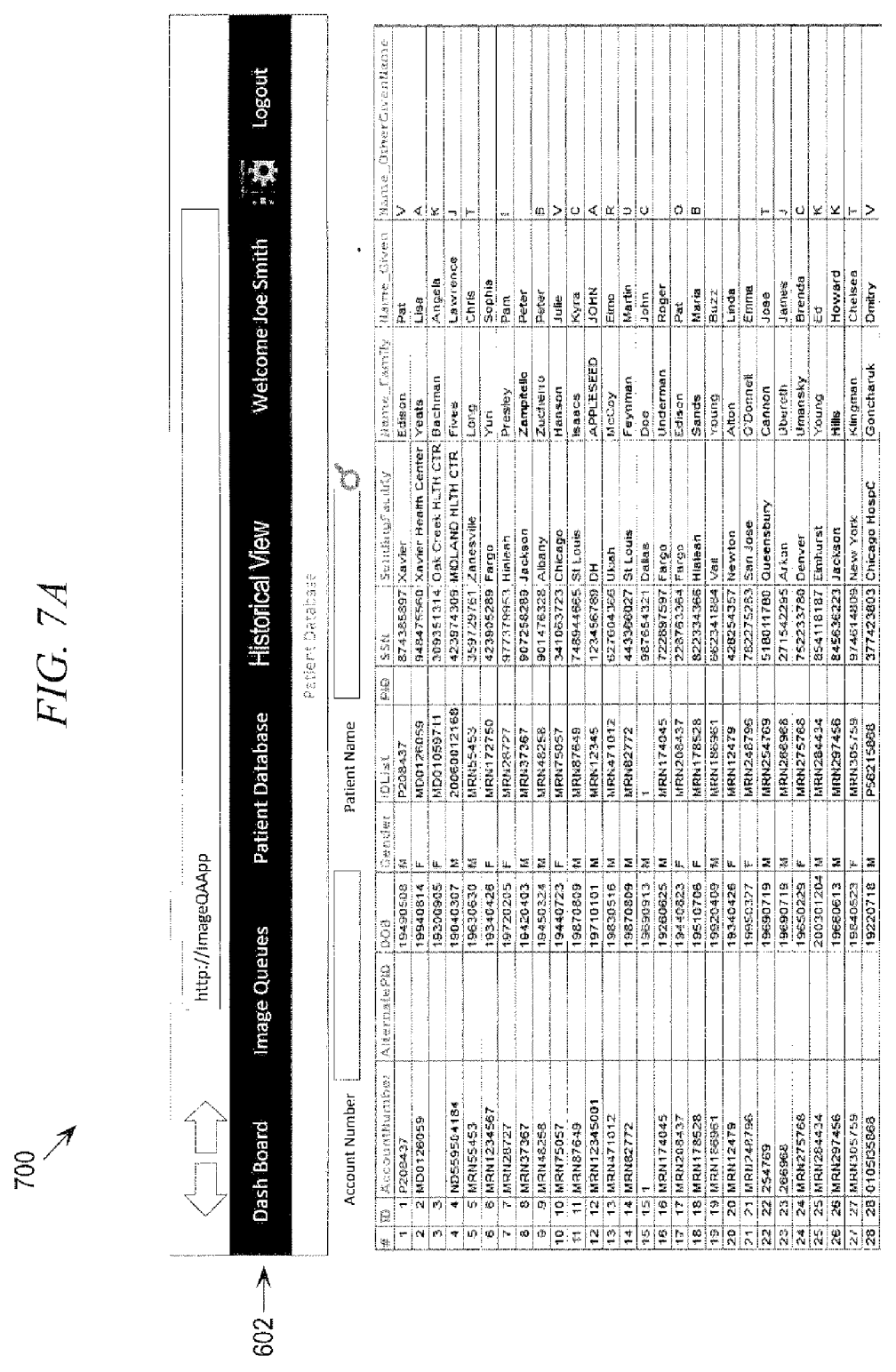
Figure 7B:
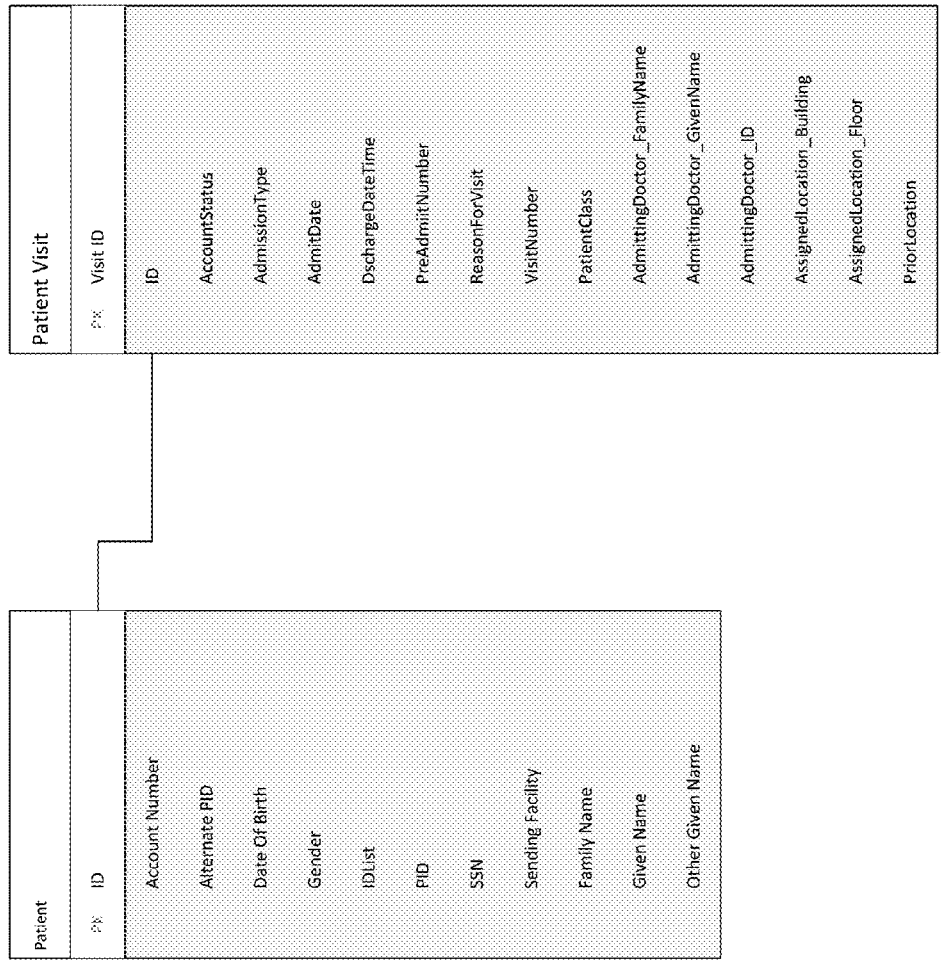
FIG. 7B is a table that depicts an example patient database schema.

FIG. 7A is a table 700 that depicts an example patient database, where each row of the table 700 corresponds to a patient and specifies an identifier, a date of birth (DOB), a gender, an ID list, a social security number (SSN), a sending facility, a family name, a first (given) name and another given (middle) name. Table 700 may be displayed in response to a user selecting the "Patient Database" control 612. FIG. 7B is a table 750 that depicts an example patient database schema.

VI. Historical Views

According to one embodiment, images are displayed to a user using a historical view. In general, a historical view displays a sequence of images that includes a reference image and one or more other images acquired using the reference image as a background image as described herein.

Figure 8:
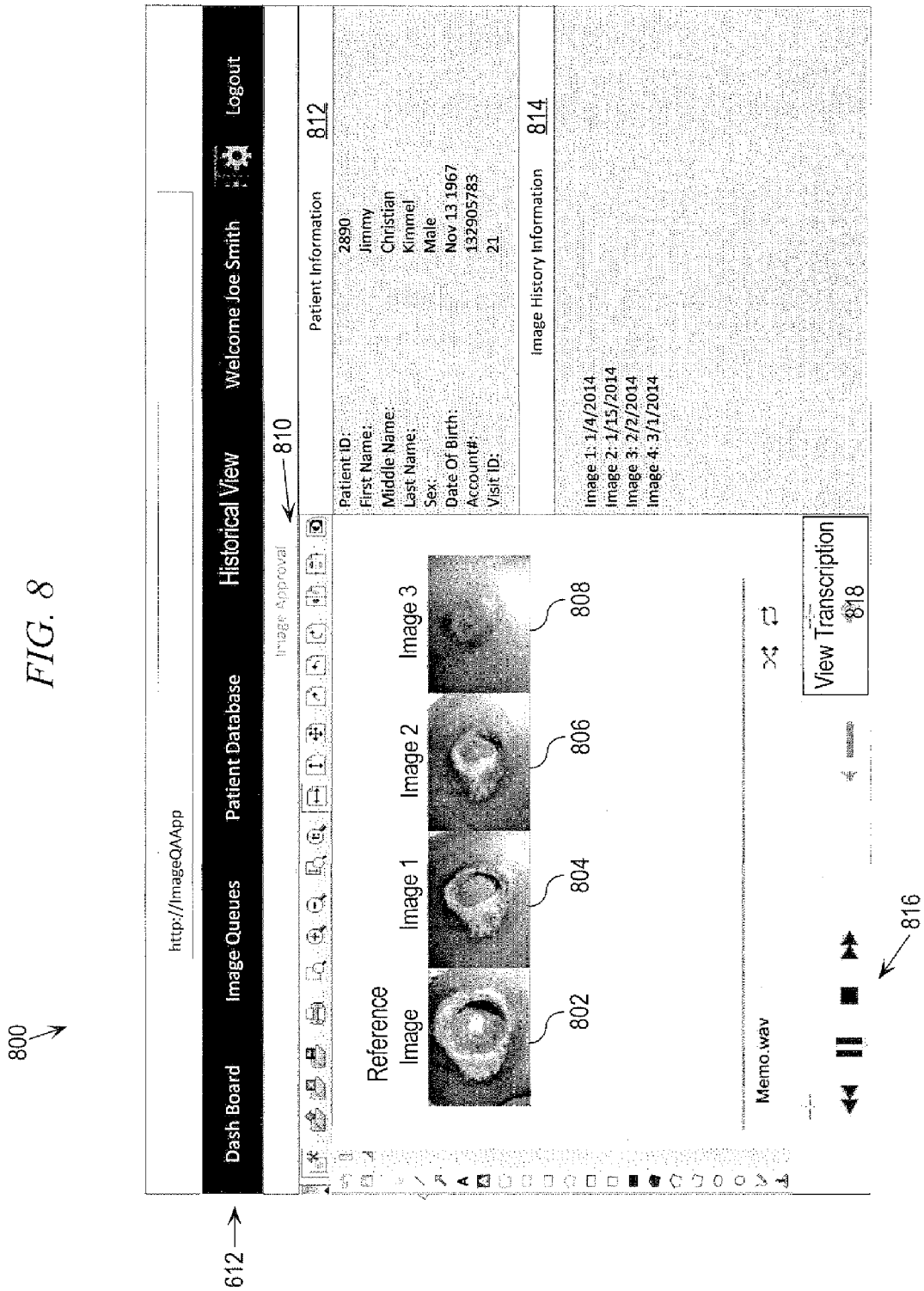
FIG. 8 depicts an example historical view screen generated by image management application.

FIG. 8 depicts an example historical view screen 800 generated by image management application 164 according to an embodiment. A user of client device 110 may access image management application 164 and request access to a historical view of images, for example, by selecting the "Historical View" control 612. In response to this request, image management application 164 may provide access to historical view screen 800. As one non-limiting example, historical view screen 800 may be represented by one or more Web pages provided by image management application 164 to client device 110.

In the example depicted in FIG. 8, historical view screen 800 includes a plurality of graphical user interface objects that include graphical user interface controls 612 that provide access to the dashboard, the image queues and the patient database previously described herein. The historical view screen 800 includes a sequence of images 802-808 of one or more objects selected by a user. When the historical view screen 800 is first displayed, a user may be shown a collection of image sequences, where each image sequence is represented by one or more graphical user interface objects, such as an icon, textual description, thumbnail image or other information. The user selects a graphical user interface object, for example an icon, which corresponds to a particular image sequence of interest, and the images in the particular sequence are displayed.

One or more graphical user interface controls may be provided to arrange the image sequences by a time of information selected, e.g., user identification, organization, event, subject, date/time, etc. The graphical user interface controls may also allow a user to enter particular criteria and have the image sequences that correspond to the particular criteria be displayed. In the example depicted in FIG. 8, the images 802-808 correspond to a particular patient identified in patient information 812. Each image sequence includes the reference image and one or more subsequent images acquired using the reference image, as previously described herein. Note that in the example depicted in FIG. 8, multiple image sequences may be provided for a single user, i.e., a single patient. For example, suppose that a patient sustained injuries on two locations of their body, e.g., an arm and a leg. In this example, one image sequence may correspond to the patient's arm and another image sequence may correspond to the patient's leg.

The images 802-808 include a reference image 802 and three subsequent images acquired using the reference image 802, namely, Image 1 804, Image 2 806 and Image 3 808. In this example, Image 1 804, Image 2 806 and Image 3 808 were acquired using the reference image 802 displayed on the mobile device 102 as a background image, as previously described herein. In addition, the images 802-808 are arranged on historical view screen 800 in chronological order, based upon the timestamp or other associated metadata, starting with the reference image 802, followed by Image 1 804, Image 2 806 and Image 3 808.

Historical view screen 800 also includes controls 810 for managing displayed images 802-808 and information about a user that corresponds to the images 802-808, which in the present example is represented by patient information 812. Image history information 814 displays metadata for images 802-808. In the example depicted in FIG. 8, the metadata includes a date at which each image 802-808 was acquired, but the metadata may include other data about images 802-808, for example, a distance at which the images were acquired 802-808, timestamps, memorandum data, etc. Metadata may also be displayed near or on a displayed image. For example, the timestamp that corresponds to each image 802-808 may be superimposed on, or be displayed adjacent to, each image 802-808.

Controls 816 allow a user to play an audio recording that corresponds to the displayed image and a control 818 allows a user to view an alphanumeric transcription of the audio recording that corresponds to the displayed image.

The historical view approach for displaying a sequence of images that includes a reference image and one or more other images that were acquired using the reference image as a background image and at approximately the same distance is very beneficial to see changes over time in the one or more objects captured in the images. For example, the approach allows medical personnel to view changes over time of a wound or surgical sight. As another example, the approach allows construction personnel to monitor progress of a project, or identify potential problems, such as cracks, improper curing of concrete, etc. As yet another example, the approach allows a user to monitor changes in natural settings, for example, to detect beach or ground erosion.

VII. Implementation Mechanisms

Although the flow diagrams of the present application depict a particular set of steps in a particular order, other implementations may use fewer or more steps, in the same or different order, than those depicted in the figures.

According to one embodiment, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 9:
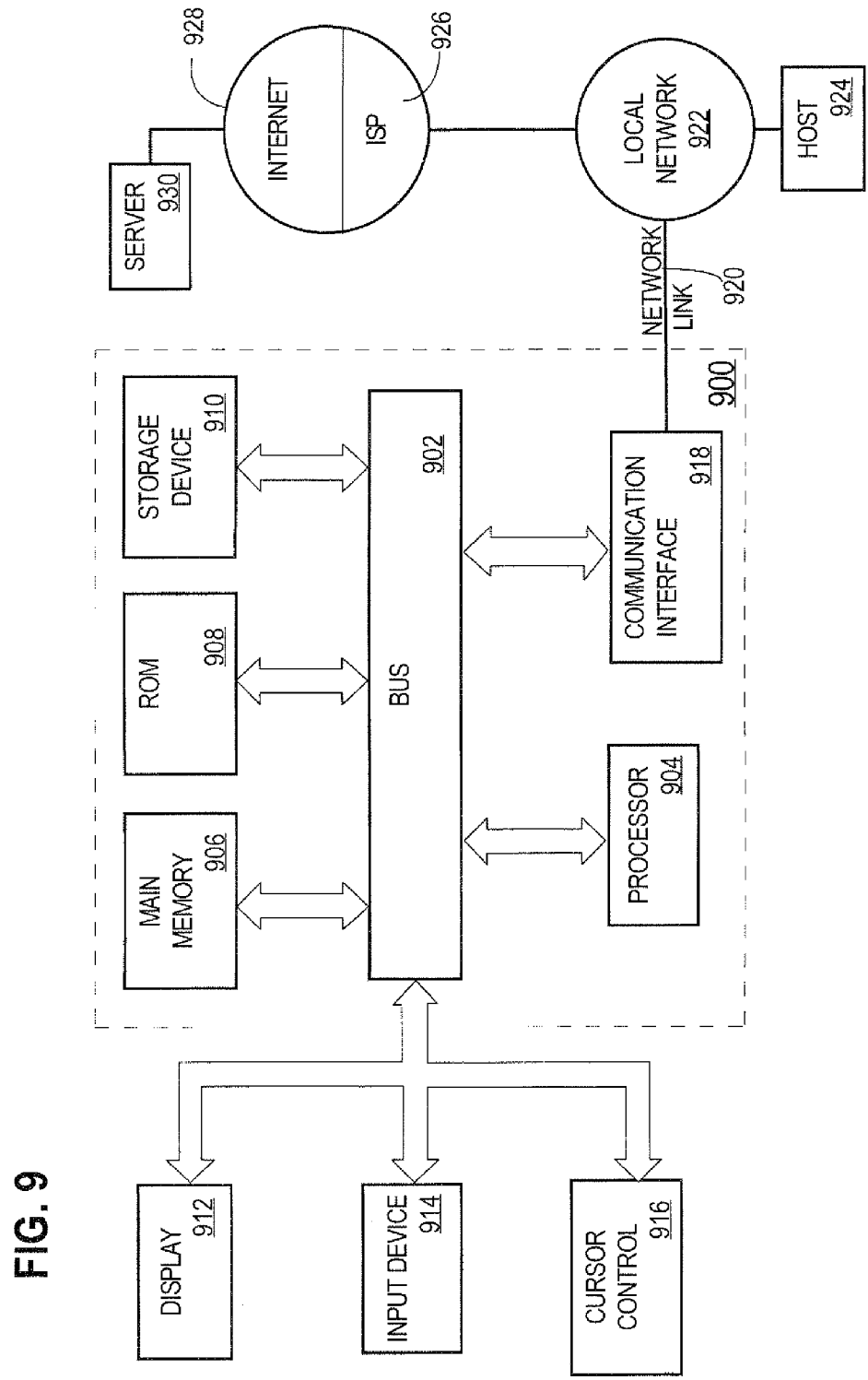
FIG. 9 is a block diagram that depicts an example computer system upon which embodiments may be implemented.

FIG. 9 is a block diagram that depicts an example computer system 900 upon which embodiments may be implemented. Computer system 900 includes a bus 902 or other communication mechanism for communicating information, and a processor 904 coupled with bus 902 for processing information. Computer system 900 also includes a main memory 906, such as a random access memory (RAM) or other dynamic storage device, coupled to bus 902 for storing information and instructions to be executed by processor 904. Main memory 906 also may be used for storing temporary variables or other intermediate information during execution of instructions to be executed by processor 904. Computer system 900 further includes a read only memory (ROM) 908 or other static storage device coupled to bus 902 for storing static information and instructions for processor 904. A storage device 910, such as a magnetic disk or optical disk, is provided and coupled to bus 902 for storing information and instructions.

Computer system 900 may be coupled via bus 902 to a display 912, such as a cathode ray tube (CRT), for displaying information to a computer user. Although bus 902 is illustrated as a single bus, bus 902 may comprise one or more buses. For example, bus 902 may include without limitation a control bus by which processor 904 controls other devices within computer system 900, an address bus by which processor 904 specifies memory locations of instructions for execution, or any other type of bus for transferring data or signals between components of computer system 900.

An input device 914, including alphanumeric and other keys, is coupled to bus 902 for communicating information and command selections to processor 904. Another type of user input device is cursor control 916, such as a mouse, a trackball, or cursor direction keys for communicating direction information and command selections to processor 904 and for controlling cursor movement on display 912. This input device typically has two degrees of freedom in two axes, a first axis (e.g., x) and a second axis (e.g., y), that allows the device to specify positions in a plane.

Computer system 900 may implement the techniques described herein using customized hard-wired logic, one or more ASICs or FPGAs, firmware and/or program logic or computer software which, in combination with the computer system, causes or programs computer system 900 to be a special-purpose machine. According to one embodiment, those techniques are performed by computer system 900 in response to processor 904 processing instructions stored in main memory 906. Such instructions may be read into main memory 906 from another computer-readable medium, such as storage device 910. Processing of the instructions contained in main memory 906 by processor 904 causes performance of the functionality described herein. In alternative embodiments, hard-wired circuitry may be used in place of or in combination with software instructions to implement the embodiments. Thus, embodiments are not limited to any specific combination of hardware circuitry and software.

The term "computer-readable medium" as used herein refers to any medium that participates in providing data that causes a computer to operate in a specific manner. In an embodiment implemented using computer system 900, various computer-readable media are involved, for example, in providing instructions to processor 904 for execution. Such a medium may take many forms, including but not limited to, non-volatile media and volatile media. Non-volatile media includes, for example, optical or magnetic disks, such as storage device 910. Volatile media includes dynamic memory, such as main memory 906. Common forms of computer-readable media include, without limitation, a floppy disk, a flexible disk, hard disk, magnetic tape, or any other magnetic medium, a CD-ROM, any other optical medium, a RAM, a PROM, and EPROM, a FLASH-EPROM, any other memory chip, memory cartridge or memory stick, or any other medium from which a computer can read.

Various forms of computer-readable media may be involved in storing instructions for processing by processor 904. For example, the instructions may initially be stored on a storage medium of a remote computer and transmitted to computer system 900 via one or more communications links. Bus 902 carries the data to main memory 906, from which processor 904 retrieves and processes the instructions. The instructions received by main memory 906 may optionally be stored on storage device 910 either before or after processing by processor 904.

Computer system 900 also includes a communication interface 918 coupled to bus 902. Communication interface 918 provides a communications coupling to a network link 920 that is connected to a local network 922. For example, communication interface 918 may be a modem to provide a data communication connection to a telephone line. As another example, communication interface 918 may be a local area network (LAN) card to provide a data communication connection to a compatible LAN. Wireless links may also be implemented. In any such implementation, communication interface 918 sends and receives electrical, electromagnetic or optical signals that carry digital data streams representing various types of information.

Network link 920 typically provides data communication through one or more networks to other data devices. For example, network link 920 may provide a connection through local network 922 to a host computer 924 or to data equipment operated by an Internet Service Provider (ISP) 926. ISP 926 in turn provides data communication services through the world wide packet data communication network now commonly referred to as the "Internet" 928. Local network 922 and Internet 928 both use electrical, electromagnetic or optical signals that carry digital data streams.

Computer system 900 can send messages and receive data, including program code, through the network(s), network link 920 and communication interface 918. In the Internet example, a server 930 might transmit a requested code for an application program through Internet 928, ISP 926, local network 922 and communication interface 918. The received code may be processed by processor 904 as it is received, and/or stored in storage device 910, or other non-volatile storage for later execution.

In the foregoing specification, embodiments have been described with reference to numerous specific details that may vary from implementation to implementation. Thus, the sole and exclusive indicator of what is, and is intended by the applicants to be, the invention is the set of claims that issue from this application, in the specific form in which such claims issue, including any subsequent correction. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A mobile device comprising:
   a camera;
   a distance detection mechanism;
   a display;
   one or more processors;
   one or more memories communicatively coupled to the one or more processors; and
   an image acquisition application executing on the mobile device, wherein the image acquisition application is configured to:
   cause a reference image of one or more objects to be displayed, on the display of the mobile device, as a background image in a manner that allows a user of the mobile device to simultaneously view one or more preview images of the one or more objects currently in a field of view of the camera,
   cause the one or more preview images of the one or more objects currently in a field of view of the camera to be displayed simultaneously with the reference image on the display of the mobile device,
   cause the distance detection mechanism to detect a current distance between the camera and the one or more objects currently in the field of view of the camera,
   cause to be displayed on the display of the mobile device, both a distance at which the reference image of the one or more objects was acquired and the current distance between the camera and the one or more objects currently in the field of view of the camera;
   provide an indication to the user of the mobile device whether the current distance is within a specified amount of a distance at which the reference image was acquired, and
   in response to a user request to acquire an image, cause the camera to acquire a second image of the one or more objects.

2. The mobile device of claim 1, wherein the image acquisition application is configured to cause the reference image of one or more objects to be displayed, on the display of the mobile device, as a background image in a manner that allows a user of the mobile device to simultaneously view one or more preview images of the one or more objects currently in a field of view of the camera by changing one or more attribute values for the reference image.

3. The mobile device of claim 2, wherein the one or more attribute values for the reference image correspond to one or more attributes that include one or more of brightness, color or special effects.

4. The mobile device of claim 1, wherein the image acquisition application is configured to provide an indication to the user of the mobile device whether the camera is currently located within a specified amount of a distance at which the reference image was acquired by one or more of causing a visual indication to be displayed on the display of the mobile device or causing the mobile device to make one or more audible sounds.

5. The mobile device of claim 1, wherein the image acquisition application is further configured to:
 determine a current distance between the camera and the one or more objects currently in the field of view of the camera, and
 record distance data that specifies the current distance between the camera and the one or more objects currently in the field of view of the camera.

6. The mobile device of claim 1, wherein the image acquisition application is configured to, in response to a user request, generate and store in the one or more memories of the mobile device one or more of memorandum data or audio data.

7. The mobile device of claim 1, wherein the image acquisition application is configured to, in response to a user request, generate and store an audio recording in the one or more memories of the mobile device.

8. One or more non-transitory computer-readable media storing instructions which, when processed by one or more processors, cause:
 an image acquisition application executing on a mobile device to:
  cause a reference image of one or more objects to be displayed, on the display of the mobile device, as a background image in a manner that allows a user of the mobile device to simultaneously view one or more preview images of the one or more objects currently in a field of view of the camera,
  cause the one or more preview images of the one or more objects currently in a field of view of the camera to be displayed simultaneously with the reference image on the display of the mobile device,
  cause the distance detection mechanism to detect a current distance between the camera and the one or more objects currently in the field of view of the camera,
  cause to be displayed on the display of the mobile device, both a distance at which the reference image of the one or more objects was acquired and the current distance between the camera and the one or more objects currently in the field of view of the camera;
  provide an indication to the user of the mobile device whether the current distance is within a specified amount of a distance at which the reference image was acquired, and
  in response to a user request to acquire an image, cause the camera to acquire a second image of the one or more objects.

9. The one or more non-transitory computer-readable media of claim 8, wherein the image acquisition application causes the reference image of one or more objects to be displayed, on the display of the mobile device, as a background image in a manner that allows a user of the mobile device to simultaneously view one or more preview images of the one or more objects currently in a field of view of the camera by changing one or more attribute values for the reference image.

10. The one or more non-transitory computer-readable media of claim 9, wherein the one or more attribute values for the reference image correspond to one or more attributes that include one or more of brightness, color or special effects.

11. The one or more non-transitory computer-readable media of claim 8, wherein the image acquisition application provides an indication to the user of the mobile device whether the camera is currently located within a specified amount of a distance at which the reference image was acquired by one or more of causing a visual indication to be displayed on the display of the mobile device or causing the mobile device to make one or more audible sounds.

12. The one or more non-transitory computer-readable media of claim 8, further comprising additional instructions which, when processed by the one or more processors, cause the image acquisition application to:
 determine a current distance between the camera and the one or more objects currently in the field of view of the camera, and
 record distance data that specifies the current distance between the camera and the one or more objects currently in the field of view of the camera.

13. The one or more non-transitory computer-readable media of claim 8, further comprising additional instructions which, when processed by the one or more processors, cause the image acquisition application to, in response to a user request, generate and store in the one or more memories of the mobile device one or more of memorandum data or audio data.

14. The one or more non-transitory computer-readable media of claim 8, further comprising additional instructions which, when processed by the one or more processors, cause the image acquisition application to, in response to a user request, generate and store an audio recording in the one or more memories of the mobile device.

15. A computer-implemented method comprising:
 causing an image acquisition application executing on a mobile device to:
  cause a reference image of one or more objects to be displayed, on the display of the mobile device, as a background image in a manner that allows a user of the mobile device to simultaneously view one or more preview images of the one or more objects currently in a field of view of the camera,
  cause the one or more preview images of the one or more objects currently in a field of view of the camera to be displayed simultaneously with the reference image on the display of the mobile device,
  cause the distance detection mechanism to detect a current distance between the camera and the one or more objects currently in the field of view of the camera,
  cause to be displayed on the display of the mobile device, both a distance at which the reference image of the one or more objects was acquired and the current distance between the camera and the one or more objects currently in the field of view of the camera;
  provide an indication to the user of the mobile device whether the current distance is within a specified amount of a distance at which the reference image was acquired, and in response to a user request to acquire an image, cause the camera to acquire a second image of the one or more objects.

16. The computer-implemented method of claim 15, wherein the image acquisition application causes the reference image of one or more objects to be displayed, on the display of the mobile device, as a background image in a manner that allows a user of the mobile device to simultaneously view one or more preview images of the one or more objects currently in a field of view of the camera by changing one or more attribute values for the reference image.

17. The computer-implemented method of claim 16, wherein the one or more attribute values for the reference image correspond to one or more attributes that include one or more of brightness, color or special effects.

18. The computer-implemented method of claim 15, wherein the image acquisition application provides an indication to the user of the mobile device whether the camera is currently located within a specified amount of a distance at which the reference image was acquired by one or more of causing a visual indication to be displayed on the display of the mobile device or causing the mobile device to make one or more audible sounds.

19. The computer-implemented method of claim 15, further comprising causing the image acquisition application to:
   determine a current distance between the camera and the one or more objects currently in the field of view of the camera, and
   record distance data that specifies the current distance between the camera and the one or more objects currently in the field of view of the camera.

20. The computer-implemented method of claim 15, further comprising causing the image acquisition application to, in response to a user request, generate and store in the one or more memories of the mobile device one or more of memorandum data or audio data.

* * * * *